(12) United States Patent
Supp et al.

(10) Patent No.: US 10,495,565 B2
(45) Date of Patent: Dec. 3, 2019

(54) ENVIRONMENTAL TEST CHAMBER WITH UNIFORM AIRFLOW

(71) Applicant: Weiss Technik North America, Inc., Grand Rapids, MI (US)

(72) Inventors: Paul C. Supp, San Jose, CA (US); Sean S. McKendry, Alto, MI (US); Benjamin J. DeJager, Grand Rapids, MI (US)

(73) Assignee: Weiss Technik North America, Inc., Grand Rapids, MI (US)

( * ) Notice: Subject to any disclaimer, the term of this patent is extended or adjusted under 35 U.S.C. 154(b) by 117 days.

(21) Appl. No.: 15/549,504

(22) PCT Filed: Sep. 19, 2016

(86) PCT No.: PCT/IB2016/055589
§ 371 (c)(1),
(2) Date: Aug. 8, 2017

(87) PCT Pub. No.: WO2017/195007
PCT Pub. Date: Nov. 16, 2017

(65) Prior Publication Data
US 2018/0321131 A1 Nov. 8, 2018

Related U.S. Application Data

(60) Provisional application No. 62/335,198, filed on May 12, 2016.

(51) Int. Cl.
*G01N 17/00* (2006.01)
*F25B 39/02* (2006.01)
(Continued)

(52) U.S. Cl.
CPC .......... *G01N 17/002* (2013.01); *F25B 39/02* (2013.01); *F25B 13/00* (2013.01); *F25B 39/028* (2013.01); *F25B 41/00* (2013.01)

(58) Field of Classification Search
CPC ..... G01N 17/00; G01N 17/002; G01M 99/00; G01M 99/002
(Continued)

(56) References Cited

U.S. PATENT DOCUMENTS 4,967,155 A 10/1990 Magnuson
5,792,419 A 8/1998 Williamson et al.
(Continued)

OTHER PUBLICATIONS

International Search Report of the International Searching Authority from corresponding Patent Cooperation Treaty (PCT) Application No. PCT/IB2016/055589, indicated completed on Jan. 6, 2017.
(Continued)

*Primary Examiner* — Benjamin R Schmitt
(74) *Attorney, Agent, or Firm* — Gardner, Linn, Burkhart & Ondersma LLP (57) ABSTRACT

An environmental test chamber, and method of testing a response of a unit-under-test to treated air, includes a housing having an enclosing wall defining a test bay with an access opening in the wall providing access to the test bay and a closure selectively covering the opening. An airflow plenum supplies treated air to the test bay. An air treatment system treating air flowing through the plenum. A control operates the air treatment system to flow treated air through the plenum in two selective modes. The air treatment system flows treated air in a first flow direction through the test bay in one of the modes and flows air in a second flow direction through the test bay in a second of the modes. The first and second flow directions are different from each other.

21 Claims, 12 Drawing Sheets

(51) Int. Cl.
*F25B 13/00* (2006.01)
*F25B 41/00* (2006.01)

(58) Field of Classification Search
USPC .......................................................... 73/865.6
See application file for complete search history.

(56) References Cited

U.S. PATENT DOCUMENTS

| | | |
|---|---|---|
| 6,272,767 B1 | 8/2001 | Botruff et al. |
| 6,679,128 B2 | 1/2004 | Wanek et al. |
| 7,337,630 B2 | 3/2008 | Yanik et al. |
| 7,992,454 B2 | 8/2011 | Purdy et al. |
| 8,294,587 B2 | 10/2012 | Danz et al. |
| 8,616,063 B2 | 12/2013 | Provost et al. |
| 2009/0151370 A1 | 6/2009 | Immink |
| 2014/0083211 A1* | 3/2014 | Moon ...................... G01N 1/28 73/863.11 |
| 2015/0176865 A1 | 6/2015 | McDonnell et al. |

OTHER PUBLICATIONS

Written Opinion of the International Searching Authority from corresponding Patent Cooperation Treaty (PCT) Application No. PCT/IB2016/055589, indicated completed on Jan. 6, 2017.

\* cited by examiner

ENVIRONMENTAL TEST CHAMBER WITH UNIFORM AIRFLOW

CROSS REFERENCE TO RELATED APPLICATIONS

The present application is a 371 national phase application of PCT Application No. PCT/IB2016/055589, filed Sep. 19, 2016, which claims priority to U.S. provisional patent application Ser. No. 62/335,198 filed May 12, 2016, the disclosure of which are hereby incorporated herein by reference in their entireties.

BACKGROUND OF THE INVENTION

The present invention is directed to an environmental test chamber and a method of testing a response of a unit-under-test to temperature differences in such environmental test chamber.

Environmental test chambers are used, for example, to qualify a piece of equipment as being capable of withstanding a variety of environmental conditions. One such type of environmental test chamber subjects the equipment to a wide range of temperatures to simulate real life transportation and use conditions. If the equipment under test performs satisfactorily after being subjected to the wide range of temperatures, it can be expected that the equipment will perform in real life conditions.

SUMMARY OF THE INVENTION

It is common for units-under-test to be supplied with cables in order to operate the units to simulate real-life operating conditions. Some units-under-test, such as electronic servers or other electronic units, are powered during thermal testing in order to simulate operating conditions. With a large number of units in a test rack, the operator typically positions the units-under-test in a manner most convenient to supply the wiring to the units. However, the orientation of the units-under-test can affect performance of the test especially where the units-under test have their own cooling fans. Also, if the flow rate of treated air is too high, the treated air can pressurize the unit-under-test thus creating an air curtain effect so that the treated air cools the units, not their own fan. The present invention supplied treated air at a relatively high volume and low flow rate in a direction that matches the orientation of the fan of the unit-under-test so that unused treated air washes past the unit-under-test and is not forced through it. Also, by aligning direction of treated airflow with the fans of the units-under-test, the heat given off by the unit-under-test is not recirculated over the unit. Therefore, the test more closely replicates performance of the unit-under-test in its use environment.

An environmental test chamber, according to an aspect of the invention, includes a housing having an enclosing wall defining a test bay with an access opening in the wall providing access to the test bay and a closure selectively covering the opening. An airflow plenum supplies treated air to the test bay. An air treatment system treats air flowing through the plenum. A control operates the air treatment system to flow treated air through the plenum in two selective modes. The air treatment system flows treated air in a first flow direction through the test bay in one of the modes and flows air in a second flow direction through the test bay in a second of the modes. The first and second flow directions are different from each other.

The first and second flow directions may be generally opposite from each other. The air treatment system may include one or more fans. The fan(s) is reversible between the first and second flow directions. The fan(s) may include a reversible motor and a plurality of bi-directional axial flow blades. The motor may be a variable speed motor in order to provide variable speed of treated air. The plenum may extend generally from top to bottom of the test bay and have an air grill at one end of the test bay and another air grill at an opposite end of the test bay. The air grill may be adjacent the access opening and the other air grill opposite the access opening.

The air treatment system may include a refrigeration system having an evaporator coil and a fluid circuit for routing refrigerant through the evaporator coil. The fluid circuit may include a first fluid circuit portion that is configured to optimize cooling of air flowing in one direction through the evaporator coil and a second fluid circuit portion that is configured to optimize cooling of air flowing in a second opposite direction through the evaporator coil. The first fluid circuit portion may be configured to flow refrigerant in a direction through the evaporator coil and the second fluid circuit portion configured to flow refrigerant in a second opposite direction through the evaporator coil. The first fluid circuit portion may alternate with the second fluid circuit portion horizontally and vertically in the evaporator coil. The evaporator coil may be made up of at least one or more evaporator coils each in the plenum on opposite sides of the fan(s).

A method of testing a response of a unit-under-test to temperature differences in an environmental test chamber, according to an aspect of the invention, includes operating an air treatment system to flow treated air through a plenum in two selective modes. The air treatment system flows treated air in a first flow direction through the unit-under-test in one of the modes and flows air in a second flow direction through the unit-under-test in a second of the modes. The first and second flow directions being different from each other.

The unit-under-test may have a cooling fan and further includes selecting the one of the selective modes according to the orientation in the test bay of the cooling fan of the unit-under-test. Treated air may be supplied below a rate that would force treated air through the unit-under-test. The air treatment system may provide treated air at selectable flow rates.

These and other objects, advantages and features of this invention will become apparent upon review of the following specification in conjunction with the drawings.

DESCRIPTION OF THE PREFERRED EMBODIMENT

Figure 1:
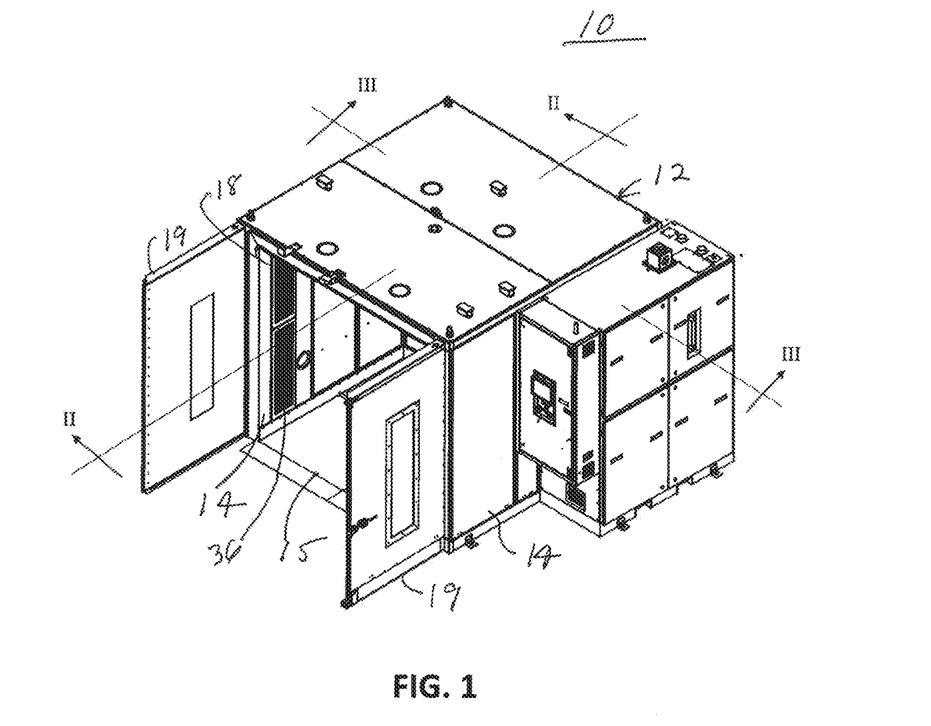
FIG. 1 is a perspective view of an environmental test chamber, according to an embodiment of the invention.
Figure 2:
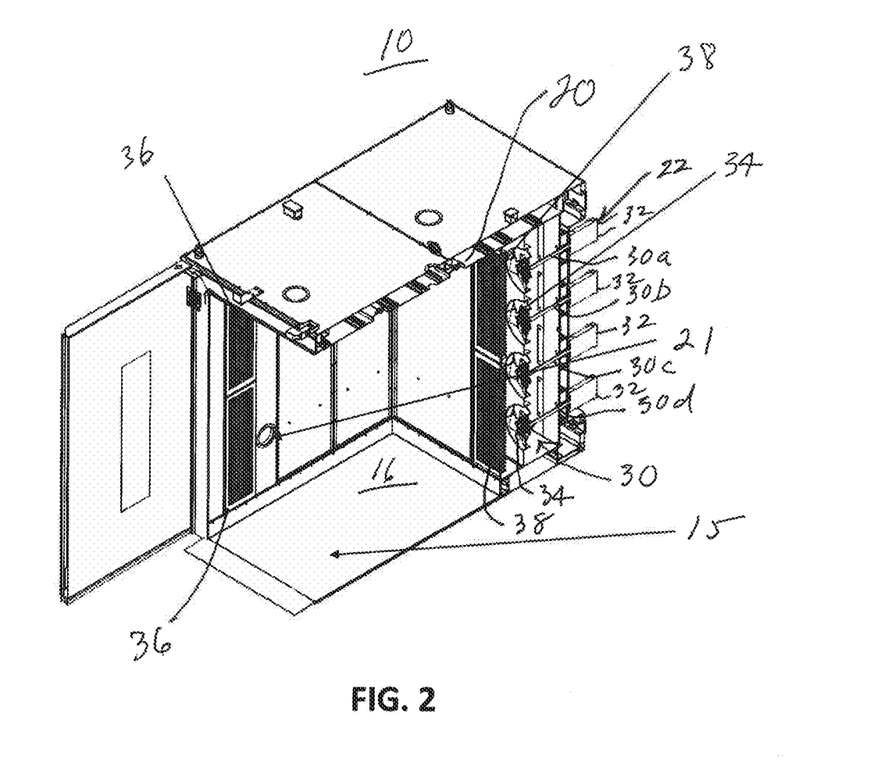
FIG. 2 is a sectional view taken along the lines II-II in FIG. 1.
Figure 3:
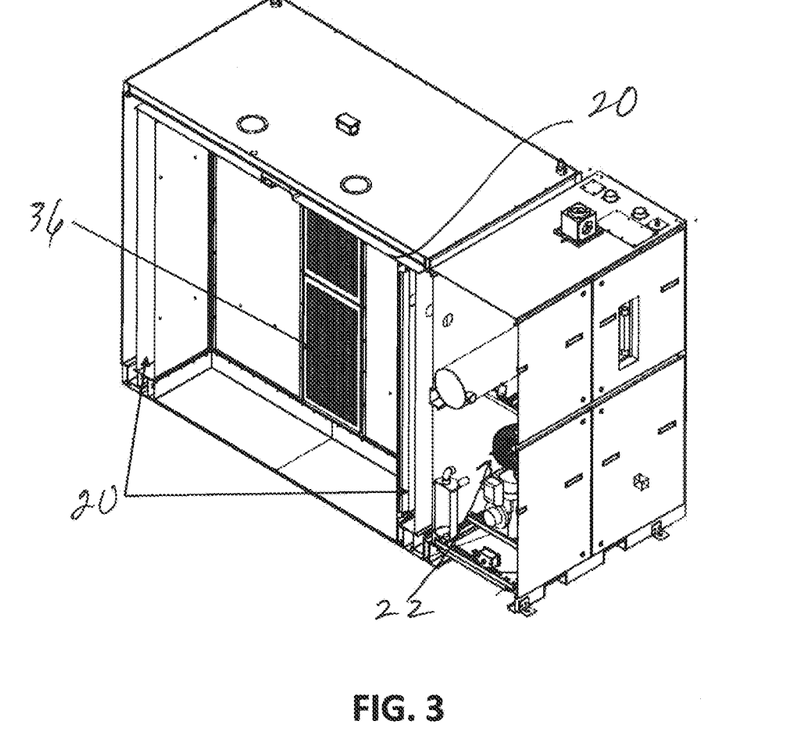
FIG. 3 is a sectional view taken along the lines III-III in FIG. 1.
Figure 4:
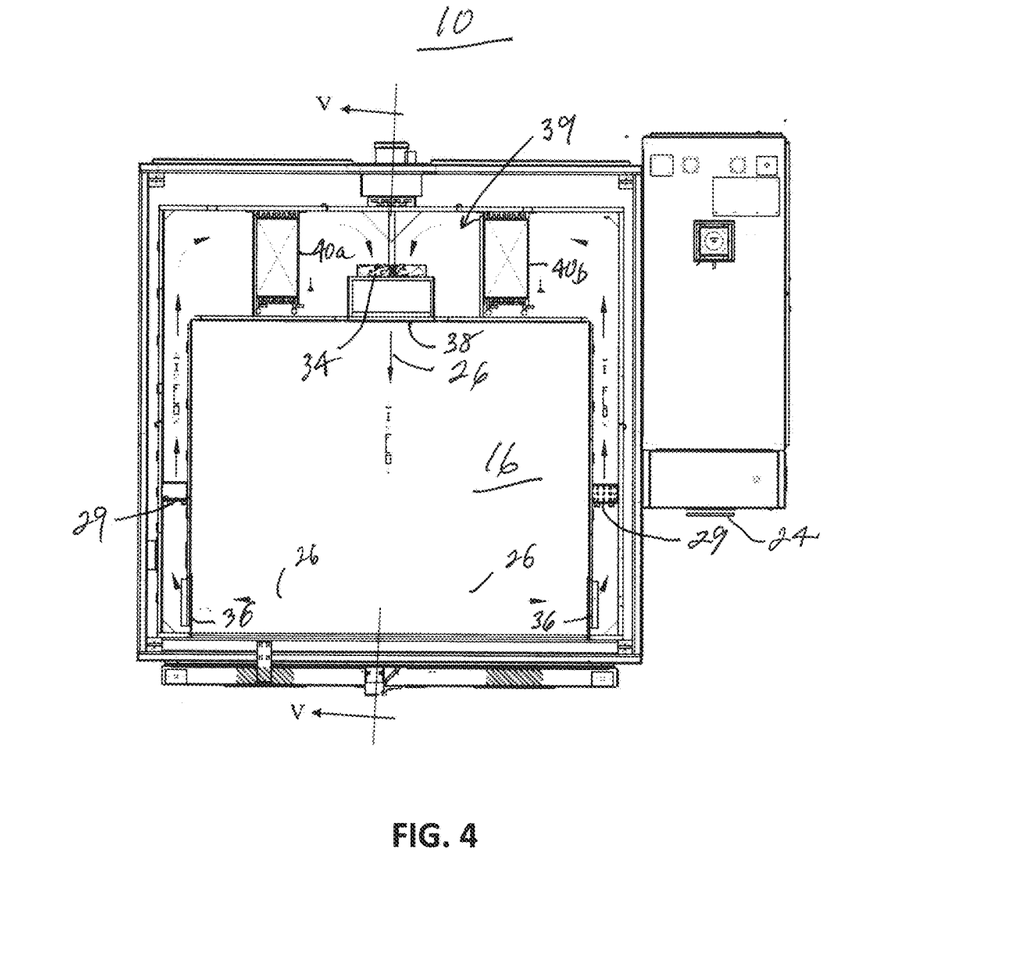
FIG. 4 is a top plan view of the interior of the environmental test chamber in FIG. 1 illustrating airflow in a first direction through the chamber.
Figure 5:
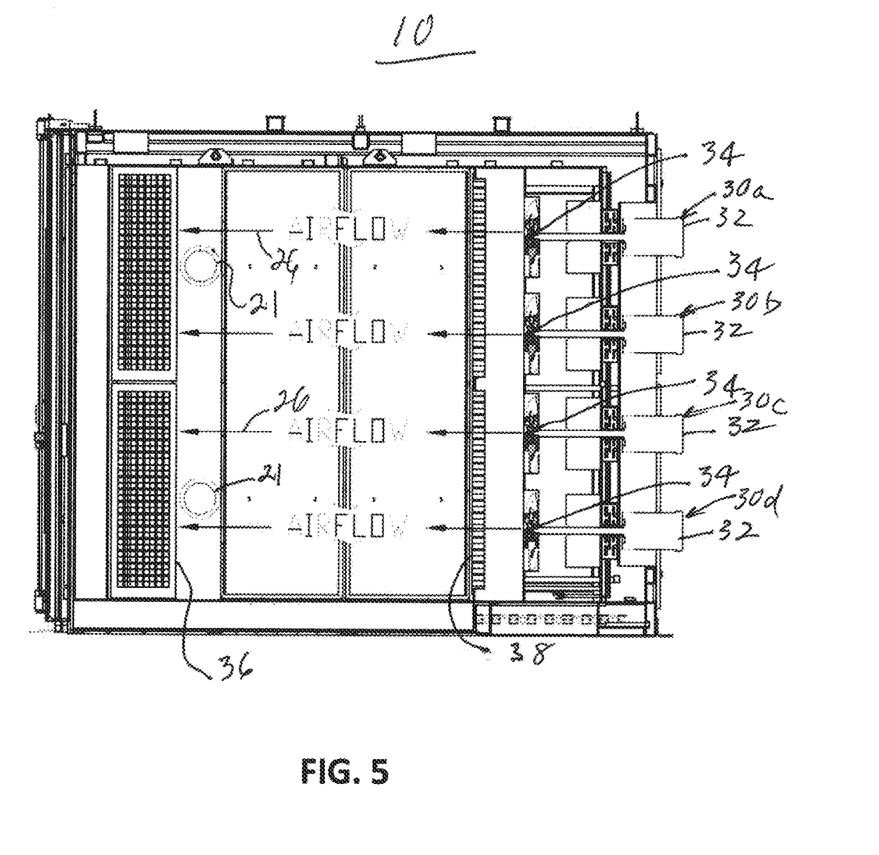
FIG. 5 is a sectional view taken along the lines V-V in FIG. 4.
Figure 6:
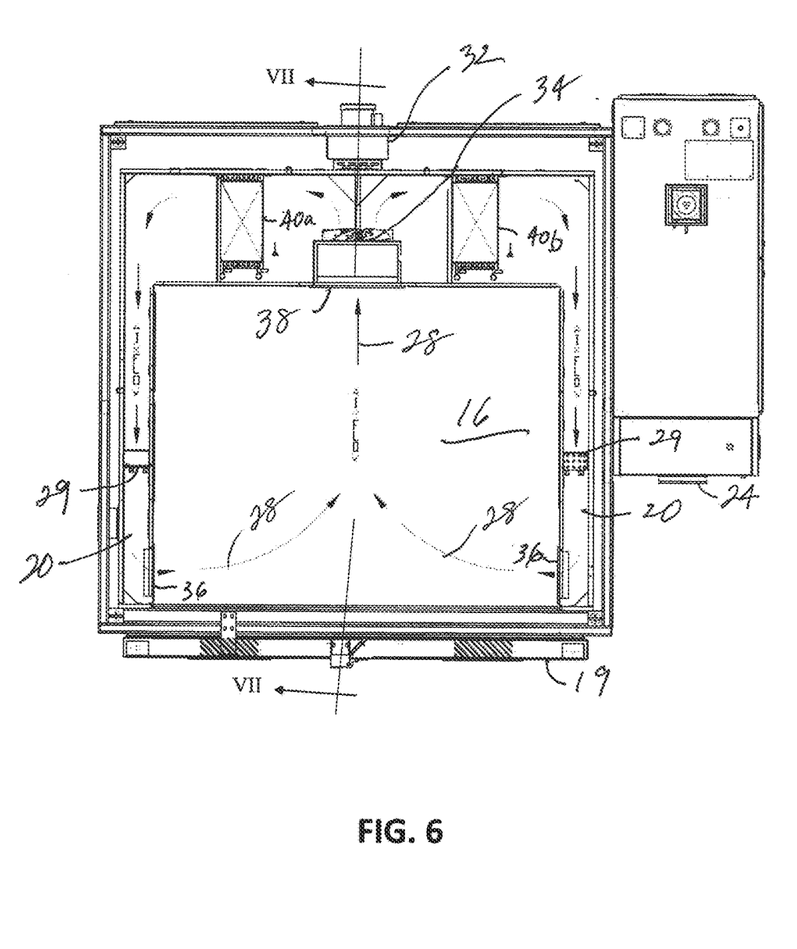
FIG. 6 is a top plan view of the interior of the environmental test chamber in FIG. 1 illustrating airflow in a second direction that is opposite to the airflow illustrated in FIG. 4.
Figure 7:
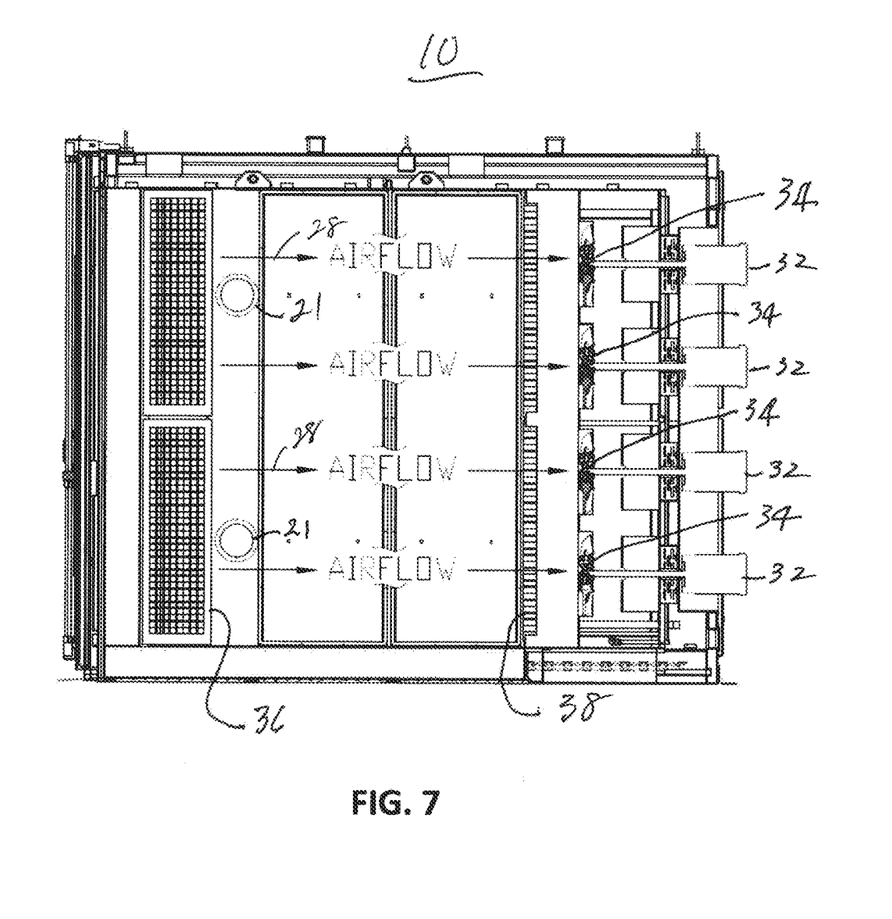
FIG. 7 is a sectional view taken along the lines VII-VII in FIG. 6.

Referring now to the drawings and the illustrative embodiments depicted therein, an environmental test chamber 10 includes a housing 12 having an enclosing wall 14 and floor 15 defining a test bay 16. An access opening 18 in wall 14 provides access to test bay 16 for an operator. A closure, such as a door 19, selectively covers opening 18 and includes one or more gaskets (not shown) to resist air leakage from test bay 16 when door 19 is shut. One or more equipment access openings 21 may be provided in wall 14 to allow cabling, or the like, to be supplied to the units-under-test. An airflow plenum 20 supplies treated air to test bay 16. An air treatment system, generally shown at 22, treats air flowing through plenum 20. Air treatment system 22 typically raises or lowers air temperature, but can also increase or decrease humidity. A control 24 operates air treatment system 22 to flow treated air through plenum 20 in two user selectable modes. Air treatment system 22 is selectable to flow treated air in a first flow direction 26 through test bay 16 in one of the modes, as illustrated in FIGS. 4 and 5. Air treatment system 22 flows air in a second flow direction 28 through test bay 16 in a second of said modes, as illustrated in FIGS. 6 and 7. As can be seen by comparing FIGS. 4 and 5 with FIGS. 6 and 7, first and second flow directions 26 and 28 are different from each other, in general, and, in particular, the first and second flow directions are generally opposite from each other.

Air treatment system 22 includes at least one fan 30 and, in the illustrated embodiment, includes 4 commonly controlled fans 30a, 30b, 30c and 30d. Fans 30a-30d are reversible between said first and second flow directions 26, 28. This is accomplished in the illustrative embodiment by fans 30a-30d, each being driven by a reversible motor 32. Each fan also includes a plurality of bi-directional axial flow blades 34. In this manner, fans 30a-30d are capable of causing airflow in the first and second airflow directions, by reversing motor direction, and are capable of flowing air at approximately the same efficiency in both airflow directions because of the configuration of bi-directional axial flow blades 34. At least one fan 30 is capable of producing variable air flow. While this could be accomplished by switching one or more fans 30a-30d off or on, this is accomplished in the illustrated embodiment by each motor 32 being a variable speed motor in order for fans 30a-30d to provide variable speed of treated air.

Plenum 20 extends generally from top-to-bottom along both sides of test bay 16 and may even extend along the ceiling and/or floor of the housing in order to provide the highest possible air volume flow for a given air speed and plenum thickness. One or more sets of air openings, such as grills 36, are at one end of the test bay connected with one end of plenum 20 and another set of air openings, such as grill 38, are at an opposite end of the test bay 16 adjacent fan blades 34. Air grill(s) 36 are adjacent access opening 18 on opposite sides thereof. Air grill 38 is opposite access opening 18. For airflow direction 26, treated air is discharged from air grill 38 through the test bay and then returned through grill(s) 36. For airflow direction 28, treated air is discharged from grill(s) 36 through the test bay and then returned through grill 38. Grill(s) 36 and/or 38 may have adjustable louvers to assist in directing flow of treated air. The grill(s) may have various opening sizes and/or shapes including perforated holes, or the like.

Figure 8:
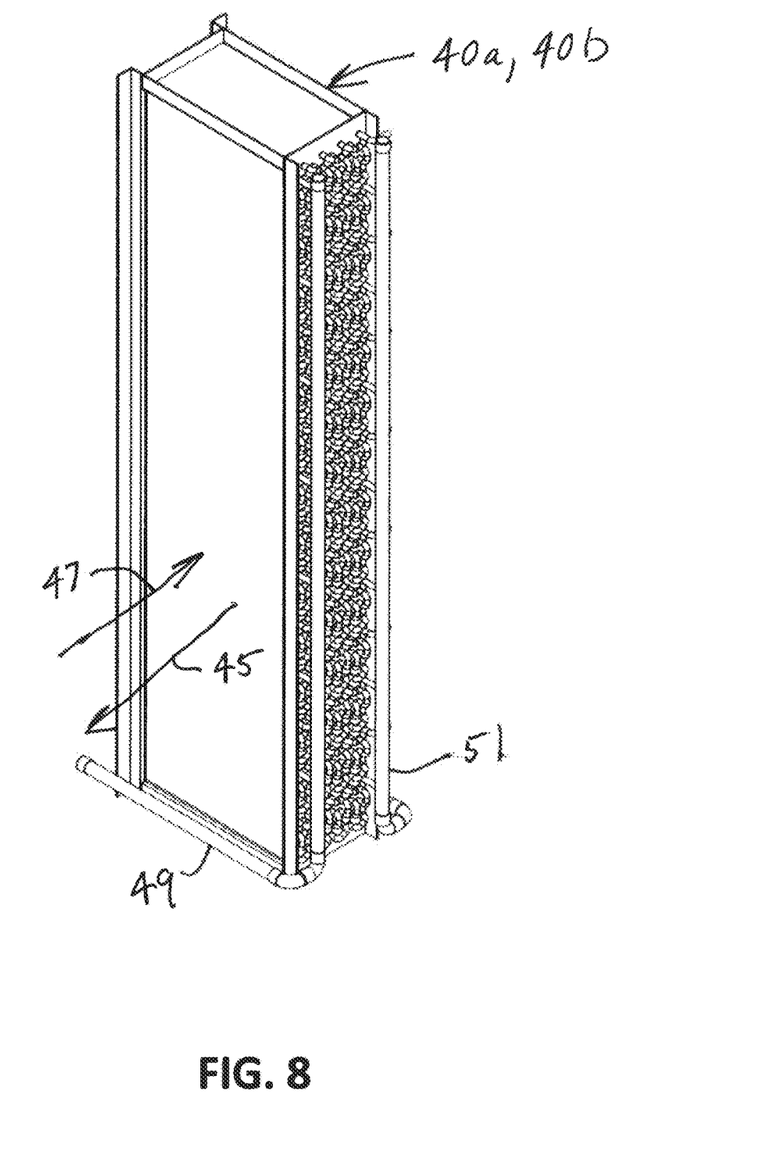
FIG. 8 is a perspective view of an evaporator.
Figure 9:
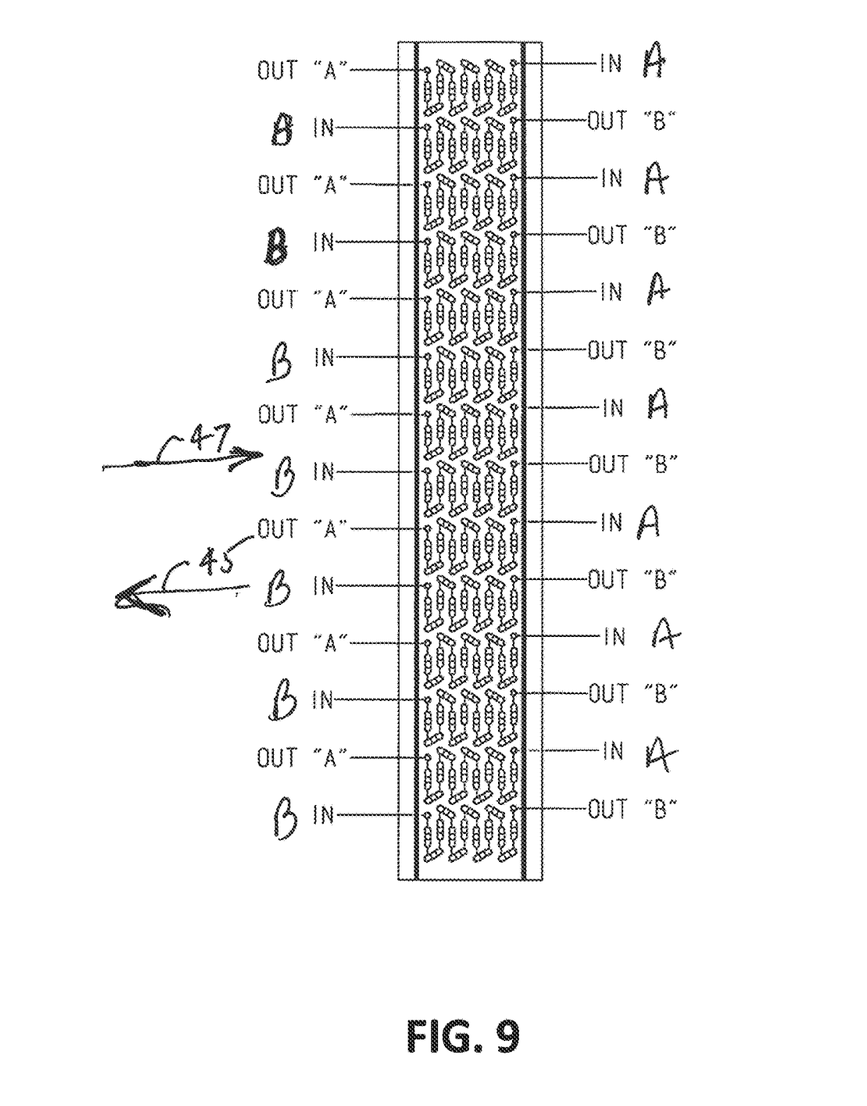
FIG. 9 is a side elevational view of the evaporator in FIG. 8.
Figure 10:
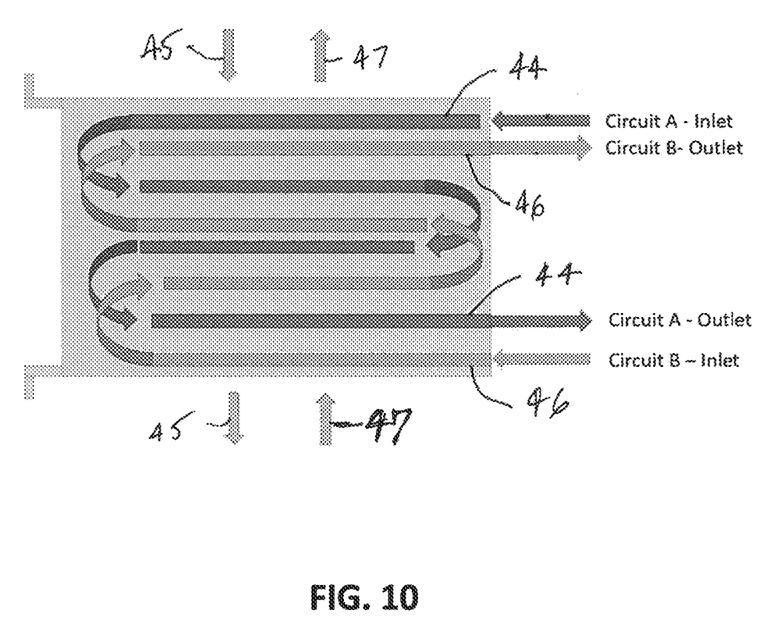
FIG. 10 is a top plan view of the evaporator in FIG. 8 showing a schematic diagram of refrigerant flow.

Air treatment system 22 includes a refrigeration system 39 having an evaporator coil assembly made up of one or more evaporator coils 40a, 40b and a fluid circuit for routing refrigerant through an evaporator coil 40a, 40b. Evaporator coil(s) 40a, 40b are positioned in plenum 20 on opposite sides of fan 30. Therefore, air will flow over one coil(s) 40a, 40b irrespective of whether the air travels to the left or right side of plenum 20. The fluid circuit includes a first fluid circuit portion 44 that is configured to optimize cooling of air flowing one direction 45 through evaporator coil 40a, 40b and a second fluid circuit portion 46 that is configured to optimize cooling of air flowing a second opposite direction 47 through evaporator coil 40a. 40b. First fluid circuit portion 44 is configured to flow refrigerant in a direction through evaporator coil 40a, 40b, and second fluid circuit portion 46 is configured to flow refrigerant in a second opposite direction through evaporator coil 40a, 40b, as best seen in FIG. 10. This can best be accomplished by arranging a fluid inlet for one fluid circuit portion, labelled as "circuit A," adjacent an outlet for the other fluid circuit portion, labelled as "circuit B." As can best be seen in FIG. 9, the layout of circuits A and B alternate both horizontally and also in the vertical direction of the evaporator coil in order to further optimize cooling of the airflow through both directions 45 and 47. Also, a suction line 49 can be connected as a header for all outlets A, and a suction line 51 can be connected as a header for outlets B. Similar liquid lines may be connected with all inlets A and all inlets B. Air treatment system 22 also includes a mechanism to heat air. In the illustrated embodiment, such heating mechanism is a pair of electric heaters 29. However, other techniques are possible for heating treated air, such as an operating refrigeration system in a heat pump mode in which heat is discharged by evaporator coil assembly 40 acting as a condenser.

In use, a unit-under-test (not shown) is arranged in test bay 16 in a manner most optimal for the operator. This may be arranged, for example, with the cabling between units-under-test oriented toward access opening 18 in order for convenient access to the units for connecting the cabling. Since each unit-under-test has a cooling fan that may direct cooling air toward the cabling or away from the cabling depending on the configuration of the unit-under-test, the operator adjusts the control 24 to direct airflow to one of the first airflow directions 26 or airflow directions 28 to have airflow in the test bay coincide with airflow produced by the unit-under-test cooling fan. Also, the operator adjusts air speed produced by fan 30 so that the cooling fan of the unit-under-test moves air at a faster speed than the air speed of treated air in the test bay. In this manner, the treated air in the chamber is not artificially cooling the unit-under-test. Also, the treated air washes past the unit-under-test thereby increasing the capability to test a greater number of units-under-test. Also, the units-under-test do not become pressurized by a high rate of treated airflow. In this manner, a more realistic test of the units-under-test can be performed to simulate operation of the equipment in real-life operating condition.

Figure 11:
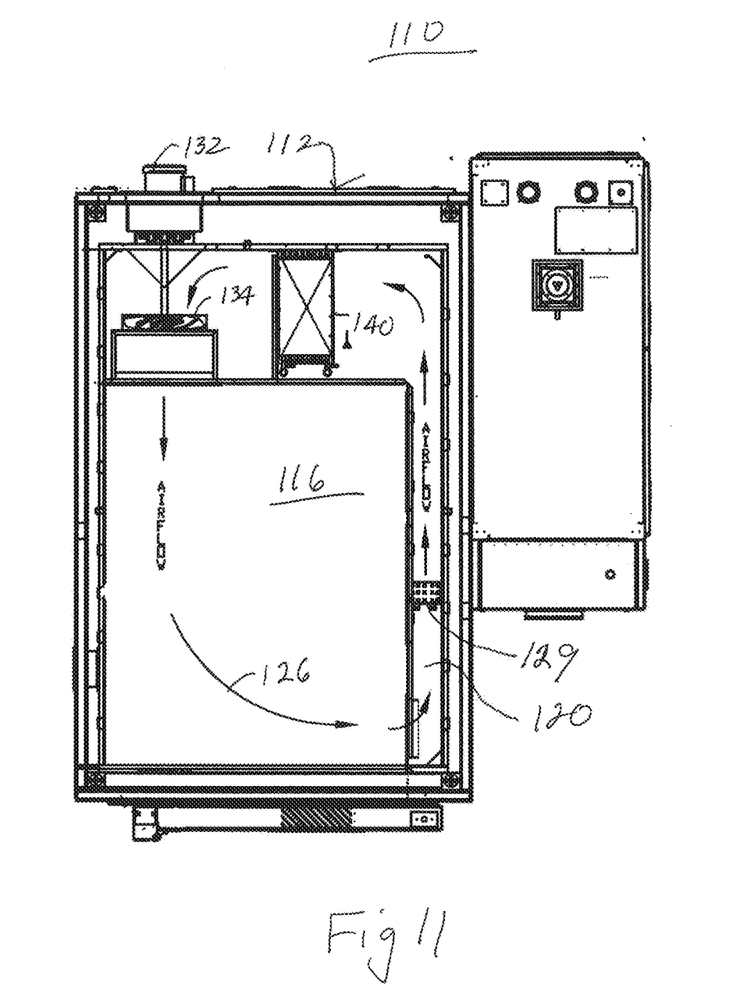
FIG. 11 is a top plan view of an alternative embodiment of an environmental test chamber illustrating airflow in a first direction through the chamber.
Figure 12:
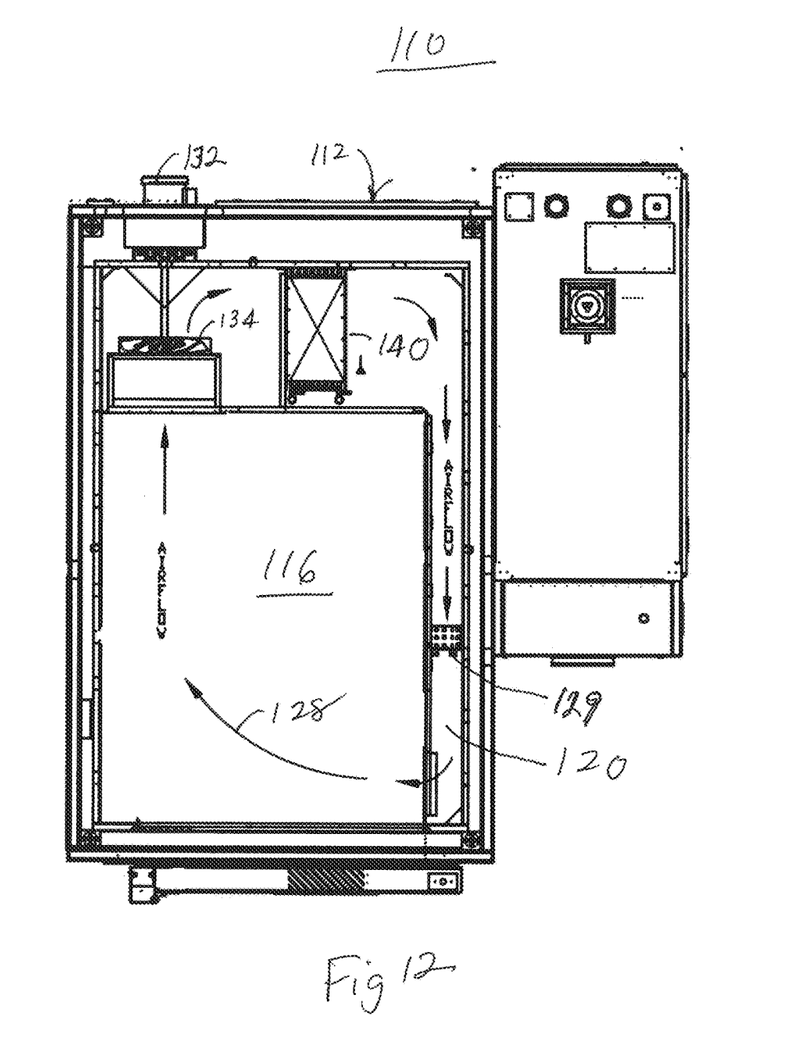
FIG. 12 is the same view as FIG. 11 illustrating airflow in a second direction through the chamber.

An alternative environmental test chamber 110 includes a housing 112 with a wall 114 defining a test by 116 and an airflow plenum 120 (FIGS. 11 and 12). Environmental test chamber 110 is otherwise the same as test chamber 10 except that it includes only one evaporator coil 140, one heater 129, and plenum 120 is along one side of the chamber. However, fan 130 operated by reversible variable speed motor 132 is capable of flowing air in a first flow direction 126, shown in FIG. 11, or a second opposite airflow direction 128, shown in FIG. 12. Other variations will be apparent to the skilled artisan.

While not illustrated, other test equipment, such as vibration tables, humidification systems, dehumidification systems, water spray devices, product cycling fixtures, and the like, can be positioned in test bay 16 or plenum 20 to provide additional tests to the units-under-test. While the foregoing description describes several embodiments of the present invention, it will be understood by those skilled in the art that variations and modifications to these embodiments may be made without departing from the spirit and scope of the invention, as defined in the claims below. The present invention encompasses all combinations of various embodiments or aspects of the invention described herein. It is understood that any and all embodiments of the present invention may be taken in conjunction with any other embodiment to describe additional embodiments of the present invention. Furthermore, any elements of an embodiment may be combined with any and all other elements of any of the embodiments to describe additional embodiments.

The embodiments of the invention in which an exclusive property or privilee is claimed are defined as follows:

1. An environmental test chamber, comprising:
   a housing having an enclosing wall defining a test bay with an access opening in said wall providing access to said test bay and a closure selectively covering said opening;
   an airflow plenum supplying treated air to said test bay;
   an air treatment system treating air flowing through said plenum; and
   a control, said control operating said air treatment system to flow treated air through said plenum in two selective modes, wherein said air treatment system flows treated air in a first flow direction through said test bay in one of the modes and flows air in a second flow direction through said test bay in a second of the modes, wherein said first and second flow directions being different from each other wherein the control is adapted to receive a selection of the mode of operating of the air treatment system based at least in part upon orientation in the test bay of a unit-under-test.

2. The environmental test chamber as claimed in claim 1 wherein the first and second flow directions being generally opposite from each other.

3. The environmental test chamber as claimed in claim 1 wherein said air treatment system includes at least one fan, said at least one fan being reversible between the first and second flow directions.

4. The environmental test chamber as claimed in claim 3 wherein said at least one fan comprises a plurality of fans.

5. The environmental test chamber as claimed in claim 3 wherein said at least one fan comprises a reversible motor and a plurality of bi-directional axial flow blades.

6. The environmental test chamber as claimed in claim 3 wherein said at least one fan comprises a variable speed motor in order to provide variable speed of treated air.

7. The environmental test chamber as claimed in claim 1 wherein said plenum extends generally from top to bottom of said test bay and has air openings at one end of the test bay and other air openings at an opposite end of the test bay.

8. The environmental test chamber as claimed in claim 7 wherein said air openings are adjacent said access opening and said other air openings are opposite said access opening.

9. The environmental test chamber as claimed in claim 7 wherein said air openings comprise a grill and said other air openings comprise another grill.

10. An environmental test chamber, comprising:
    a housing having an enclosing wall defining a test bay with an access opening in said wall providing access to said test bay and a closure selectively covering said opening;
    an airflow plenum supplying treated air to said test bay;
    an air treatment system treating air flowing through said plenum;
    a control, said control operating said air treatment system to flow treated air through said plenum in two selective modes, wherein said air treatment system flows treated air in a first flow direction through said test bay in one of the modes and flows air in a second flow direction through said test bay in a second of the modes, wherein said first and second flow directions being different from each other; and wherein said air treatment system comprises a refrigeration system having an evaporator coil and a fluid circuit for routing refrigerant through said evaporator coil, wherein said fluid circuit includes a first fluid circuit portion that is configured to optimize cooling of air flowing in said first flow direction through said evaporator coil and a second fluid circuit portion that is configured to optimize cooling of air flowing in said second flow direction through said evaporator coil.

11. The environmental test chamber as claimed in claim 10 wherein said first fluid circuit portion is configured to flow refrigerant in a first refrigerant flow direction through said evaporator coil and said second fluid circuit portion is configured to flow refrigerant in a second opposite refrigerant flow direction through said evaporator coil.

12. The environmental test chamber as claimed in claim 10 wherein said first fluid circuit portion alternates with said second fluid circuit portion horizontally and vertically in said evaporator coil.

13. The environmental test chamber as claimed in claim 10 wherein said evaporator coil comprises at least one evaporator coil in said plenum on a side of at least one fan.

14. A method of testing a response of a unit-under-test to treated air in an environmental test chamber, comprising:
    the environmental test chamber having a housing, an airflow plenum and an air treatment system, said housing having an enclosing wall defining a test bay with an access opening in said wall providing access to said test bay and a closure selectively covering said opening, said airflow plenum supplying treated air to said test bay and said air treatment system treating air flowing through said plenum; and
    operating said air treatment system to flow treated air through said plenum in two selective modes, wherein said air treatment system flows treated air in a first flow direction through the unit-under-test in one of said modes and flows air in a second flow direction through the unit-under-test in a second of said modes, wherein said first and second flow directions being different from each other, including selecting the mode of operating the air treatment system based at least in part upon orientation in the test bay of the unit-under-test.

15. The method of testing as claimed in claim 14 wherein the unit-under-test has a cooling fan and including selecting the one of said selective modes according to the orientation in the test bay of the cooling fan of the unit-under-test.

16. The method of testing as claimed in claim 14 wherein supplying treated air comprises supplying treated air below a rate that would force treated air through the unit-under-test.

17. The method of testing as claimed in claim 16 wherein said air treatment system provides treated air at selectable flow rates.

18. A refrigeration system for use in an environmental test chamber having a housing with an enclosing wall defining a test bay with an access opening in said wall providing access to said test bay and a closure selectively covering said opening, an airflow plenum supplying treated air to said test bay, an air treatment system treating air flowing through said plenum and a control, said control operating said air treatment system to flow treated air through said plenum in two selective modes, wherein said air treatment system flows treated air in a first flow direction through said test bay in one of the modes and flows air in a second flow direction through said test bay in a second of the modes, wherein said first and second flow directions being different from each other, wherein said air treatment system includes a refrigeration system, said refrigeration system comprising:

an evaporator coil and a fluid circuit for routing refrigerant through said evaporator coil, wherein said fluid circuit includes a first fluid circuit portion that is configured to optimize cooling of air flowing in said first flow direction through said evaporator coil and a second fluid circuit portion that is configured to optimize cooling of air flowing in said second flow direction through said evaporator coil.

19. The refrigeration system as claimed in claim 18 wherein said first fluid circuit portion is configured to flow refrigerant in a first refrigerant flow direction through said evaporator coil and said second fluid circuit portion is configured to flow refrigerant in a second opposite refrigerant flow direction through said evaporator coil.

20. The refrigeration system as claimed in claim 18 wherein said first fluid circuit portion alternates with said second fluid circuit portion horizontally and vertically in said evaporator coil.

21. The refrigeration system as claimed in claim 18 wherein said evaporator coil comprises at least one evaporator coil in said plenum on a side of at least one fan.

* * * * *